United States Patent [19]

Zeman

[11] Patent Number: 5,015,412

[45] Date of Patent: May 14, 1991

[54] ALKALINE TOLERANT SULFOBETAINE AMPHOTERIC SURFACTANTS

[75] Inventor: William J. Zeman, Janesville, Wis.

[73] Assignee: Sherex Chemical Company, Inc., Dublin, Ohio

[21] Appl. No.: 452,572

[22] Filed: Dec. 18, 1989

Related U.S. Application Data

[60] Division of Ser. No. 140,972, Jan. 5, 1988, Pat. No. 4,913,841, and a continuation-in-part of Ser. No. 732,509, May 9, 1985, abandoned.

[51] Int. Cl.[5] .......................... C07C 317/28; B01J 13/00

[52] U.S. Cl. .......................... 252/311; 252/355; 252/DIG. 7; 252/352

[58] Field of Search .......................... 252/352, 355, , 356, 252/DIG. 7, 311, DIG. 4

[56] References Cited

U.S. PATENT DOCUMENTS

| | | | |
|---|---|---|---|
| 2,697,116 | 12/1954 | Stayner | 252/355 |
| 3,225,073 | 12/1965 | Glabesch et al. | 252/355 |
| 3,280,179 | 10/1966 | Ernst | 252/DIG. 7 |
| 3,539,521 | 11/1970 | Snoddy et al. | 252/355 |
| 3,619,115 | 11/1971 | Diehl | 252/355 |
| 4,005,029 | 1/1977 | Jones | 252/DIG. 7 |
| 4,088,612 | 5/1978 | Carter et al. | 252/DIG. 7 |

FOREIGN PATENT DOCUMENTS 2331057 1/1974 Fed. Rep. of Germany .

*Primary Examiner*—Richard D. Lovering
*Assistant Examiner*—Valerie Fee
*Attorney, Agent, or Firm*—Mueller and Smith

[57] ABSTRACT

Disclosed is an aqueous basic solution having a calculated pH of 13 or greater of a sulfobetaine which is soluble and stable for extended periods of storage. The sulfobetaine also is soluble and stable in aqueous basic solutions of high concentration, e.g. up to 30%-50% by weight sodium hydroxide or potassium hydroxide.

5 Claims, No Drawings

ALKALINE TOLERANT SULFOBETAINE AMPHOTERIC SURFACTANTS

CROSS-REFERENCE TO RELATED APPLICATIONS

This application is a division of application Ser. No. 07/140,972, filed Jan. 5, 1988 now U.S. Pat. No. 4,913,841, which is a continuation-in-part application of copending application U.S. Ser. No. 06/732,509, filed May 9, 1985, now abandoned, the disclosure of which is incorporated expressly herein by reference.

BACKGROUND OF THE INVENTION

The present invention relates to amphoteric surfactants and more particularly to a novel class of amphoteric surfactants which are compatible with high levels of caustic.

In a variety of cleaning and other chemical uses, use of strong basic aqueous solutions is required. Since many of these cleaning and other chemical uses also require the basic solution to exhibit surfactancy, a need exists for surface active agents or surfactants which exhibit their surface active properties when contained in strongly basic aqueous solutions.

As an additional property, such surfactants in a strongly basic alkaline solution should display very low to moderate foaming characteristics. Thus, an unusual combination of constraints are placed upon a surfactant in order to satisfy such criteria.

BROAD STATEMENT OF THE INVENTION

The present invention is directed to a class of surfactants which are soluble in strongly basic alkaline solutions (i.e. a calculated pH of 13 or greater, advantageously 15 or greater), are storage stable for extended time periods of storage in strongly basic alkaline solutions, and are very low to moderate foamers. Moreover, such surfactants retain their surfactant properties when incorporated into strongly basic aqueous solutions. The novel surfactants which possess such unique combination of properties are alkyl sulfobetaines wherein the alkyl group ranges from about 6 to 12 carbon atoms in chain length. Another aspect of the present invention is an aqueous solution (calculated pH of 13 or greater) of the alkyl sulfobetaine and a base, such as, for example, sodium hydroxide or potassium hydroxide in concentrations ranging up to 30%–50% in concentration.

Advantages of the present invention include an amphoteric surfactant which is soluble in water. Another advantage is an amphoteric surfactant which is soluble and storage stable in an aqueous basic solution having a calculated pH of 13 or higher. A further advantage is an amphoteric surfactant which retains its surfactant properties in an aqueous basic solution. Yet another advantage is an amphoteric surfactant which is stable in strongly basic aqueous solutions. These and other advantages will be readily apparent to those skilled in the art based upon the disclosure contained herein.

DETAILED DESCRIPTION OF THE INVENTION

The amphoteric sulfobetaine surfactants of the present invention are unique in their ability to meet diverse criteria required of them in formulating aqueous basic surfactant solutions having a calculated pH of 13 or greater. This high pH requirement of the present invention distinguishes the novel aqueous betaine solutions, for example, from the detergent compositions of U.S. Pat. Nos. 3,539,521 and 3,619,115 which utilize betaines having $R_1$ being $C_{12}$–$C_{18}$ and preferably $C_{14}$–$C_{16}$ at pH levels of up to 11.5–12.0. At pH levels above 13, however, the betaines lose water solubility at chain lengths of $R_1$ of 12 and greater. Thus, the $C_6$–$C_{12}$ chain length restriction of $R_1$ in the present invention. Also, the intended industrial cleaning preferred uses of the novel aqueous betaine solution dictate the much higher pH or caustic levels used in the present invention.

The sulfobetaines of the present invention can be represented conventionally by the following general structure:

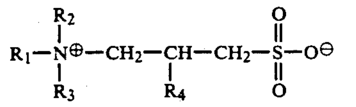

where

R is a $C_6$–$C_{12}$ alkyl group;

$R_2$ and $_3$ are a methyl group, a 2-hydroxy ethyl group, or a 2-hydroxy propyl group; and $R_4$ is H or OH.

Within the alkyl group range of about $C_6$–$C_{12}$ the sulfobetaine possesses the requisite degree of water solubility and surfactancy required of it. At chain lengths above $C_{12}$, water solubility of the sulfobetaine at high pHs becomes a problem and typically is lost (i.e. the sulfobetaine becomes insoluble in highly alkaline water). While various reaction schemes may be envisioned for synthesis of the alkyl sulfobetaines of the present invention, the following two-step reaction scheme currently is favored where $R_4$ is OH. The initial step involves the formation of an epichlorhydrin/bisulfite intermediate. This reaction conveniently is conducted in water in the presence of a base (for example, sodium hydroxide) at relatively moderate reaction temperatures (e.g. 120°–200° F.) and preferably under inert atmosphere.

Following the formation of the epichlorhydrin/bisulfite intermediate, such intermediate is reacted with the appropriate amine for forming the product sulfobetaine. This second reaction step is conducted at reaction temperatures ranging from about 100° to 200° F. Unreacted material then can be neutralized and/or removed and the pH and percent non-volatile solids of the reaction product adjusted as is necessary, desirable, or convenient in conventional fashion. For the sulfobetaine where $R_4$ is H, a propyl sultone,

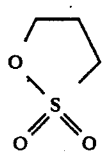

, can be reacted with the appropriate amine. The resulting alkyl sulfobetaine is soluble in caustic solution at concentrations ranging up to 10% by weight and greater. Moreover, such solubility is present even at elevated levels of potassium hydroxide, sodium hydroxide,or like bases ranging in concentrations of greater than 30%, advantageously 30%–50%, and preferably 40%–50%. Based upon the definition of pH, a theoretical maximum value of just in excess of about 15.5 is possible. It will be appreciated, though, that discussions of pH become less meaningful at these ultra-high levels of caustic. Also, use of sodium or potassium hydroxide becomes quite preferred in order to reach the foregoing caustic concentration.

A variety of bases may be used in conjunction with the sulfobetaines of the present invention. Such bases include, for example, sodium hydroxide, potassium hydroxide, calcium hydroxide, calcium oxide, sodium metasilicate, tetrapotassium pyrophosphate, sodium tripolyphosphate, trisodium phosphate, potassium silicate, and the like, and even mixtures thereof. As the Examples will demonstrate, the alkyl dimethyl hydroxy sulfobetaines of the present invention are stable in potassium hydroxide and sodium hydroxide solutions ranging up to about 40–50 percent concentration.

The aqueous basic solutions of sulfobetaines of the present invention find use in a variety of applications. Such applications include for example, bottle washing compounds, hot vat cleaning compounds, paper pulping, paint strippers, railroad and aircraft cleaners, dairy and food plant cleaners, detergent sanitizers, polymer-based wax strippers, and the like. The excellent stability, surfactancy, and low foaming characteristics of the alkyl dimethyl sulfobetaine caustic solutions make them useful in these and a variety of additional applications.

The following Example shows how the present invention can be practiced but should not be construed as limiting. All percentages and proportions are by weight in this application unless otherwise expressly indicated.

EXAMPLES

Example 1

Lauryldimethyl sulfobetaine ($R_4$=OH) was made by a two-step process described herein. The first step involved the charging of a small Parr reactor with sodium bisulfite (242 g), epichlorohydrin (228 g), deionized water (910 g), and solid sodium hydroxide (2 g). The water and base were mixed and nitrogen sparged to remove dissolved oxygen prior to charging the reactor. The reactor was pressurized to 20 psi with nitrogen and heated to 125° F. at which point the reaction exothermed to a reaction temperature of 140°–150° F. The reaction was conducted for one hour and then sampled for determination of free sodium bisulfite. After the one hour reaction time, this analysis showed that the percent free sodium bisulfite was 0.2 percent. The reactor was cooled to 100° F. and the product removed as the reaction was judged to be complete.

1310 g of the thus-formed intermediate then was added to a three liter-four neck flask along with 416 g of lauryldimethyl amine. The flask was heated to 150°–160° F. and maintained at this temperature while the contents in the flask were stirred. After six hours reaction time, the contents in the flask changed from a milky liquid to a clear liquid. The reaction was continued for a total of 18 hours at which point the reaction was judged to be essentially complete. Sodium hydroxide (18 g, 50% concentration) was added to the flask and the temperature increased to 180° F. to hydrolyze unreacted epichlorohydrin/bisulfite intermediate. After two hours reaction time, the flask again was sampled and analyzed for percent free NaCl which proved to be 8.0 percent. The contents of the flask then were cooled to 100° F. and sufficient sulfuric acid (25% concentration) was added to adjust the pH to about 8–8.5. The final analysis of the lauryldimethyl hydroxy sulfobetaine is set forth below:

| Description | Results |
|---|---|
| Appearance at Room Temperature | Crystal Clear Liquid |
| Color (Gardner) | 1− |
| pH (5% in deionized water) | 8.5 |
| Percent Solids | 51.7 |
| Percent NaCl | 8.0 |

The lauryldimethyl hydroxy sulfobetaine was tested for solubility in aqueous potassium hydroxide solution. Concentrations of potassium hydroxide at 10%, 20%, 30%, 40%, and 50% solutions were formulated at percent solids content of lauryldimethyl hydroxy sulfobetaine of 1%, 3%, 5%, and 10%. The lauryldimethyl hydroxy sulfobetaine was judged to be soluble at all concentrations of sulfobetaine at all concentrations of potassium hydroxide. The lauryldimethyl hydroxy sulfobetaine then was subjected to Ross-Miles foam test at 1.0% by weight actives in 72° F. distilled water. The following foam heights were measured: initial, 205 mm; and +5 minutes, 26 mm. In 150 ppm hard (Ca) water at 1% concentration, Ross-Miles foam heights were: initial, 200 mm; and +5 minutes, 29 mm. Thus, it will be seen that the lauryldimethyl hydroxy sulfobetaine is low foaming as well as soluble in high concentrations of potassium hydroxide.

Next, the stability of the lauryldimethyl sulfobetaine to alkaline solutions was evaluated. Initial samples of the lauryldimethyl hydroxy sulfobetaine at 1%, 3%, and 5% by weight of a 50% solids solution of the sulfobetaine were established for 40% sodium hydroxide solutions. Surface tension and interfacial tension (against refined mineral oil, Nujol oil) were recorded initially, after one month storage in polyethylene bottles, and after 6 months of storage in polyethylene bottles. Samples for the tension evaluation were prepared by diluting the concentrate to 3% sodium hydroxide in deionized water for taking the measurements. The following results were recorded:

| Lauryldimethyl Sulfobetaine (% weight)* | Surface Tension and Interfacial Tension Measurements (Dynes/cm) Initial: Surface Tension | Initial: Interfacial Tension | One Month Storage: Surface Tension | One Month Storage: Interfacial Tension | Six Month Storage: Surface Tension | Six Month Storage: Interfacial Tension |
|---|---|---|---|---|---|---|
| 0 | 55.4 | 16.5 | 55.6 | 16.8 | 58.0 | — |
| 1 | 40.8 | 12.4 | 34.7 | 12.5 | 36.2 | 16.2 |
| 3 | 26.5 | 9.0 | 23.5 | 4.7 | 27.5 | 7.2 |
| 5 | 24.0 | 6.8 | 22.4 | 5.1 | 26.1 | 6.8 |

*% by weight sulfobetaine of a 50% solids solution of the sulfobetaine, 40% NaOH, which was stored and then diluted to 3% NaOH for these tests.

The above-tabulated results clearly demonstrate that the lauryldimethyl hydroxy sulfobetaine remains virtually unaffected when stored for time periods of up to six months in concentrated sodium hydroxide solutions. Thus, the lauryldimethyl hydroxy sulfobetaine has been demonstrated to be soluble in concentrated alkaline solutions, storage stable in concentrated alkaline solutions, and low foaming.

Example 2

An octyl dimethyl hydroxy sulfobetaine was made in a manner like that described in Example 1. At 5% by weight sulfobetaine, Ross-Miles foam heights in deionized water were: initial, 47 mm; and +5 minutes, 40 mm. In 150 ppm (Ca) hard water, Ross-Miles foam heights were: initial, 43 mm; and +5 minutes, 36 mm. The low foaming property of this betaine is demonstrated.

Samples of the octyl dimethyl hydroxy sulfobetaine were compounded at 1%, 0.1%, 0.025%, and 0.01% solids in deionized water for tension measurements. The following results were recorded.

| Octyl Dimethyl Hydroxy Sulfobetaine (% solids) | Surface Tension and Interfacial Tension Measurements (Dynes/cm) Surface Tension | Interfacial Tension |
|---|---|---|
| 0.01 | 57.7 | 30.5 |
| 0.025 | 45.5 | 19.3 |
| 0.1 | 28.9 | 6.4 |
| 1.0 | 23.8 | 2.4 |

These results clearly demonstrate the excellent surfactancy of the octyl dimethyl hydroxy sulfobetaine Solubility of the octyl dimethyl hydroxy sulfobetaine in the alkaline solutions was evaluated by dissolving the surfactant into a 50% NaOH solution at active levels of 1%, 3% and 5%. The following results were obtained:

| Octyl Dimethyl Hydroxy Betaine (% weight) | Surface Tension and Interfacial Tension Measurements (Dynes/cm): Initial | | 4 Day Storage | |
|---|---|---|---|---|
| | Surface Tension | Interfacial Tension | Surface Tension | Interfacial Tension |
| 1 | 43.9 | 19.4 | 39.5 | 14.1 |
| 3 | 34.4 | 11.9 | 31.4 | 9.5 |
| 5 | 30.2 | 10.1 | 29.6 | 8.3 |

Again, the novelty of the inventive sulfobetaines in high (pH of 13 or greater) caustic aqueous solutions is demonstrated.

What is claimed is:

1. A method for making a storage stable aqueous basic solution having a calculated pH of 13 or greater of a sulfobetaine and the following general structure:

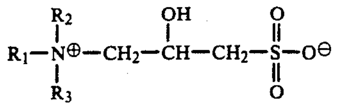

where $R_1$ is a $C_6$-$C_8$ alkyl group, $R_2$ and $R_3$ are $CH_3$, 2-hydroxy ethyl or 2-hydroxy propyl, which comprises:

(a) forming an aqueous epichlorohydrin/bisulfite intermediate;

(b) reacting said inatermediate and a $C_6$-$C_{12}$ alkyl, $R_2$, $R_3$ amine in an aqueous reaction mixture; and (c) adding sodium hydroxide to the thus-formed aqueous solution of said sulfobetaine in an amount of at least 50% by weight if not already present therein to achieve said calculated pH of greater than 13.

2. The method of claim 1 wherein $R_1$ is a $C_8$ alkyl group.

3. The method of claim 1 wherein the proportion of said sulfobetaine and said aqueous basic solution ranges from between about 0.05 and 10 percent by weight.

4. The method of claim 1 wherein said intermediate is formed at a reaction temperature of between about 120° and 200° F.

5. The method of claim 1 wherein said amine/intermediate reaction is conducted at a temperature of between about 100° and 200° F.

* * * * *